United States Patent
Heller

(10) Patent No.: US 7,186,272 B2
(45) Date of Patent: Mar. 6, 2007

(54) CONDENSATION PRODUCTS OF HYDROXYCARBOXYLIC ACIDS AND GLYCOLS OR GLYCEROL

(75) Inventor: Jürg Heller, Oberwil (CH)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 10/469,748

(22) PCT Filed: Mar. 6, 2002

(86) PCT No.: PCT/IB02/00745

§ 371 (c)(1),
(2), (4) Date: Sep. 4, 2003

(87) PCT Pub. No.: WO02/070453

PCT Pub. Date: Sep. 12, 2002

(65) Prior Publication Data

US 2004/0082808 A1    Apr. 29, 2004

(30) Foreign Application Priority Data

Mar. 8, 2001    (CH) .................................... 0428/01

(51) Int. Cl.
C08L 23/32    (2006.01)
C07C 69/66    (2006.01)
(52) U.S. Cl. ..................... 8/115.56; 560/179
(58) Field of Classification Search .............. 8/550, 8/582; 560/129, 179, 231
See application file for complete search history.

(56) References Cited

U.S. PATENT DOCUMENTS

| | | | |
|---|---|---|---|
| 2,158,107 A | 5/1939 | Carruthers et al. | 260/484 |
| 2,350,964 A * | 6/1944 | Loder et al. | 560/186 |
| 2,573,701 A | 11/1951 | Filachione et al. | 260/484 |
| 3,600,121 A | 8/1971 | Feldmann | 8/34 |
| 4,568,351 A | 2/1986 | Palleiro Cardona et al. | 8/582 |
| 5,718,732 A * | 2/1998 | Bennett et al. | 8/582 |

FOREIGN PATENT DOCUMENTS

| | | |
|---|---|---|
| CH | 669 882 | 4/1989 |
| GB | 2 302 882 | 2/1997 |

OTHER PUBLICATIONS

XP-008004387, J.T. Stearn et al., "Lactic acid as a component of synthetic resins" Industrial and Engineering Chemistry, vol. 32, 1940, pp. 1335-1342.
XP-002203586, C.E. Rehberg et al., "Mixed esters of lactic and carbonic acids. n-Alkyl carbonates of various lactates", Journal of Organic Chemistry, vol. 15, 1950, pp. 1246-1252.

* cited by examiner

Primary Examiner—Thurman K. Page
Assistant Examiner—Karl Puttlitz
(74) Attorney, Agent, or Firm—Tod A. Waldrop

(57) ABSTRACT

The invention relates to reaction products of glycols, diglycols, higher glycols or glycerol with α-hydroxycarboxylic acids in a molar ratio of 1:2 or higher, especially conforming to the general formula (V) where R is hydrogen or a $C_{1-3}$ alkyl group, preferably methyl, nx is from 1 to 5, preferably from 1 to 3, n is 1 or 2 and when n=1 the radical R" is $C_{1-4}$ alkylene, preferably ethylene, x is defined as x' and y is not less than 1, preferably from 1 to 5, especially 1 or 2, and when n=2 the radical R" is a glycerol radical, x is defined as x" and y is =1.

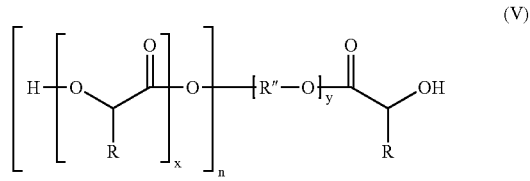

(V)

The invention further relates to the use of the (poly)hydroxycarboxylic acid (poly)glycol esters or (poly)hydroxycarboxylic acid glyceryl esters as acid donors and for controlling the pH in textile treatment processes.

13 Claims, No Drawings

CONDENSATION PRODUCTS OF HYDROXYCARBOXYLIC ACIDS AND GLYCOLS OR GLYCEROL

The invention relates to reaction products of glycols, diglycols or higher glycols and also glycerol with α-hydroxycarboxylic acids, and to the use thereof as acid donors and for controlling the pH in textile treatment processes.

Textile treatment processes generally achieve uniform treatment of the textile fibres by employing pH and/or temperature gradients instead of constant conditions. Especially the employment of a pH gradient demands an increased process engineering input, since for example acid has to be continuously metered in to lower the pH. Processes are therefore in existence in the prior art where, to avoid the metered addition of acid for example an agent is added that releases the requisite amount of acid incrementally with or without temperature increase.

CH patent 669882 utilizes reaction products of ethylene oxide with formic acid and of ethylene glycol with formic acid and isopropyl formate as acid donors. U.S. Pat. No. 4,568,351 describes reaction products of formic acid or β-hydroxycarboxylic acids with ethylene oxide for use as acid donors.

The added compounds hydrolyse during the textile finishing operation and make it possible to lower the pH of a liquor in steps. In dyeing processes for example the use of the aforementioned agents permits a slow and uniformly progressive fixation, whereby a more uniform dyeing is achieved.

JP patent 3083403 describes condensation products of hydroxyl-substituted dicarboxylic acids with alkylene glycols which are useful as levelling agents in dyeing processes for polyamide fibres. U.S. Pat. No. 3,600,121 describes esters of alkylcarboxylic acids and polyethylene glycol as retarding agents for the uniform coloration of cellulose fibres.

An important variable for determining the efficacy of the products used as acid donors and buffer compounds is the hydrolysis number. The hydrolysis number is determined as a characteristic parameter in the analysis of fats. The hydrolysis number is defined as the amount of potassium hydroxide in milligrams (mg) needed to neutralize the esterified and unesterified fatty acids contained in 1 g of fat. The hydrolysis number is thus a measure of the amount of acid which can be released from an ester by complete hydrolysis. The hydrolysis number should consequently also be determining for the trajectory of the pH curve during a textile finishing operation.

It has now been surprisingly found that the reaction of an α-hydroxycarboxylic acid conforming to the general formula (I) with a glycol, diglycol or higher glycols conforming to the general formula (II) or with glycerol in a molar ratio of 2:1 or higher leads to an unexpected trajectory of the pH curve. Of particular advantage here are condensation products of a diglycol or higher glycol with an α-hydroxycarboxylic acid in a molar ratio of 1:2 or higher, preferably 1:2, 1:3 or 1:4. Since such condensation products are generally statistical mixtures, the molar ratio need not necessarily be an integral ratio.

Useful α-hydroxycarboxylic acids conform to the general formula (I)

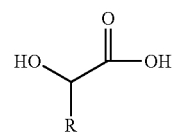

where R is hydrogen or a $C_{1-3}$ alkyl group, preferably methyl. Condensation thereof with suitable glycols, diglycols or higher glycols of the general formula (II)

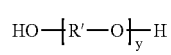

where R' is $C_{1-4}$ alkylene, preferably ethylene, and y is not less than 1, preferably from 1 to 5, especially 1 or 2, provides (poly)hydroxycarboxylic acid (poly)glycol esters of the general formula (III)

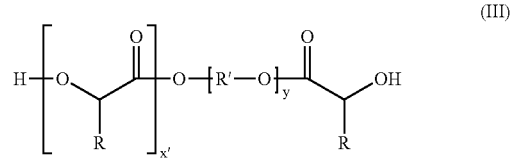

where R, R' and y are each as defined above and x' is from 1 to 5. In preferred compounds, R is a methyl group, R' is ethylene, x' is from 1 to 3 and y is from 1 to 3. Particular preference is given to compounds where x' is from 1.5 to 2 and y is 1 or 2.

Condensation of suitable α-hydroxycarboxylic acids of the general formula (I) with glycerol

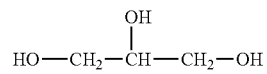

provides (poly)hydroxycarboxylic acid glyceryl esters of the general formula (IV)

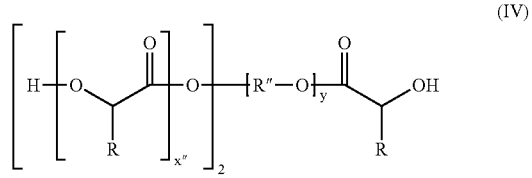

where R is as defined above, the radical R" is a glycerol radical, x" is from 0.5 to 2.5, preferably from 0.5 to 1, and y is 1. What is decisive is the ratio of y to x", so that in principle it is also possible for just two hydroxyl groups of the glycerol or for all three hydroxyl groups to be esterified with different numbers of α-hydroxycarboxylic acids. x" is to be understood as the average value of the number of condensed α-hydroxycarboxylic acids. For a molar ratio of 1:2 for glycerol to α-hydroxycarboxylic acid, x" is therefore 0.5.

The compounds are prepared by known methods. For instance, compounds of the formula (III) are obtainable by reaction of x'+1 mol of an α-hydroxycarboxylic acid conforming to the formula (I) with 1 mol of the corresponding glycol, diglycol or higher glycol of the formula (II). The reaction products can if necessary be purified after isolation.

Compounds of the formula (IV) are obtainable by reaction of 2x"+1 mol of an α-hydroxycarboxylic acid conforming to the formula (I) with 1 mol of glycerol.

Owing to their higher degree of branching, the glycerol condensation products obtained have a higher viscosity than the corresponding glycol condensation products.

The invention thus provides compounds of the formula (V)

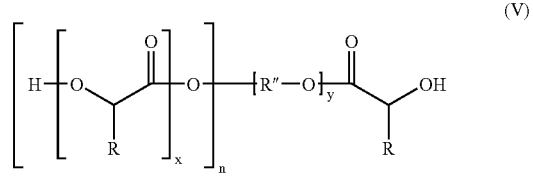

where R is hydrogen or a $C_{1-3}$ alkyl group, preferably methyl, nx is from 1 to 5, preferably from 1 to 3, n is 1 or 2 and when n=1 the radical R" is $C_{1-4}$ alkylene, preferably ethylene, x is defined as x' and y is not less than 1, preferably from 1 to 5, especially 1 or 2 and when n=2 the radical R" is a glycerol radical, x is defined as x" and y is =1.

The hydrolysis number, which should be useful as an acidity measure of esters, is unexpectedly not correlated with the molar effectiveness as an acid donor in the case of the condensation products according to the invention. On the contrary, it was surprisingly found that condensation products having a molar ratio of 1:2 or higher are more effective than prior art condensation products having a molar ratio of 1:1 in terms of the molar amount used. The compounds according to the invention are consequently of immense benefit, economically.

The compounds according to the invention may be useful as acid donors in textile finishing processes without significantly increasing the process engineering investment. The compounds according to the invention hydrolyse in the course of the textile finishing process and permit processing with variable pH at constant or variable temperatures. Generally, the abovementioned compounds are used to incrementally lower the pH of a liquor. But they can also be used for stabilizing the pH in acidic liquors in which the pH would otherwise rise in the course of the treatment operation.

More particularly, the compounds according to the invention are also useful for minimizing the changes in the pH of the liquor. This is particularly advantageous when the textile treatment agent or dye is instable to such changes.

The use as an acid donor and an agent for controlling the pH in textile treatment operations is particularly advantageous in dyeing processes for textiles made of natural, synthetic and semisynthetic fibres. Especially treatment operations under weakly alkaline or acidic conditions with constant or variable pH are of importance.

Useful natural textile materials include polyamides such as for example wool or blends of natural fibres and synthetic polyamides, for example nylon. Useful natural textile materials further include cellulose fibres, for example cotton, semisynthetic textile materials, for example cellulose acetates, and also mixtures thereof.

Useful wholly synthetic textile materials include linear aromatic polyesters, for example polyethylene terephthalates, especially the condensation products of terephthalic acid with glycols or with 1,4-bis(hydroxymethyl)cyclohexane. Further polycarbonates, for example from α,α-dimethyl-4,4'-dihydroxydiphenylmethane and phosgene, and also polyvinyl chlorides, polyacrylonitriles and polyamides.

The textile materials can be present in any conventional form, for example as fibres, yarns, webs, woven or non-woven textiles.

The compounds of the general formula (V) can be used either as such or in the form of a preparation together with emulsifiers and/or dispersants.

Preference is given to using the compounds in concentrations of 0.1 to 5 g/l, particularly preferably from 0.5 to 1 g/l.

Textile treatment processes for the purposes of the present invention are in the widest sense dyeing, printing and brightening processes and also all finishing processes in which the pH has an influence on the effect of the process. The processes in question can be continuous or batchwise.

Dyeing processes can utilize acid dyes, metal complex dyes, reactive dyes, basic dyes and disperse dyes together with the compounds and processes according to the invention.

Preferred temperature ranges are from 20 to 140° C., especially from 70–100° C.

Preferred pH ranges are between 5 and 10 at the start of the process and between 3 and 7 at the end of the process. Depending on the amount of the compound used, the pH can be kept constant or incrementally reduced. The compounds according to the invention can be added all at once or incrementally in the course of the process. An alkaline liquor can be adjusted with known agents, for example aqueous sodium hydroxide solution, sodium carbonate, borax, sodium acetate or ammonia, at the start of the process.

EXAMPLES

Preparation Example 1 (Comparative)

462 g of lactic acid (78%), 248 g of ethylene glycol and 2 g of sulphuric acid are heated to an internal temperature of 115° C. under reduced pressure and stirred at that temperature and under reduced pressure for 3 hours until distillate formation has virtually ceased.

This affords a polyester having a hydrolysis number of 406.

Preparation Example 2 (Comparative)

Example 1 is repeated to react 231 g of lactic acid (78%) with 212 g of diethylene glycol to afford a polyester having a hydrolysis number of 286.

Preparation Example 3

Example 1 is repeated to react 462 g of lactic acid (78%) with 124 g of ethylene glycol. The polyester obtained is 415 g of a yellow liquid having a viscosity of 1.4 Pas, a hydrolysis number of 529 and an $M_w$ of 279.

Preparation Example 4

600 g of lactic acid (78%), 81 g of ethylene glycol and 1 g of sulphuric acid are heated to an internal temperature of 115° C. under reduced pressure and stirred at that temperature under reduced pressure for 4 hours, during which 220 g of colourless distillate are separated off. This affords 460 g of a yellow viscous liquid (viscosity 25 Pas) having a hydrolysis number of 615 and an $M_w$ of 472.

Preparation Example 5

Example 1 is repeated to react 231 g of lactic acid (78%) with 106 g of diethylene glycol to afford a polyester having a hydrolysis number of 439 and an $M_w$ of 276.

Preparation Example 6

231 g of lactic acid (78%), 53 g of diethylene glycol and 0.5 g of sulphuric acid are heated to an internal temperature of 115° C. under reduced pressure and stirred at that temperature under reduced pressure for 3 hours, during which 84 g of water are distilled off. This affords 200 g of a yellow viscous liquid having a viscosity of 5 Pas, a hydrolysis number of 560 and an $M_w$ of 441.

Preparation Example 7

Example 1 is repeated to react 565 g of glycolic acid (70%) with 162 g of ethylene glycol to afford a polyester having a hydrolysis number of 600 and an $M_w$ of 300.

Preparation Example 8

Example 1 is repeated to react 565 g of glycolic acid (70%) with 81 g of ethylene glycol to afford a polyester having a hydrolysis number of 707 and an $M_w$ of 373.

Preparation Example 9

Example 1 is repeated to react 565 g of glycolic acid (70%) with 276 g of diethylene glycol to afford a polyester having a hydrolysis number of 502 and an $M_w$ of 257.

Preparation Example 10

Example 1 is repeated to react 565 g of glycolic acid (70%) with 138 g of diethylene glycol to afford a polyester having a hydrolysis number of 636 and an $M_w$ of 370.

Preparation Example 11 (Comparative)

Example 1 is repeated to react 231 g of lactic acid (78%) with 184 g of glycerol to afford a polyester having a hydrolysis number of 335, an $M_w$ of 246 and a viscosity of 6 Pas.

Preparation Example 12

Example 1 is repeated to react 231 g of lactic acid (78%) with 92 g of glycerol to afford a polyester having a hydrolysis number of 452, an $M_w$ of 319 and a viscosity of 28 Pas.

Preparation Example 13

Example 1 is repeated to react 231 g of lactic acid (78%) with 61 g of glycerol to afford a polyester having a hydrolysis number of 520, an $M_w$ of 374 and a viscosity of 65 Pas.

Use Examples

The following experiments were carried out to test the effectiveness of the individual condensation products as acid donors:

A certain amount of the compounds prepared according to Preparation Examples 1–8 was dissolved in 1 litre of demineralized water together with 50 mg of sodium carbonate, the resulting pH being about 10. The amount of the experimental products was chosen so that their concentration in the solution corresponded to a hydrolysis number of 425/1. This was followed by heating at a rate of 1°/min from 30° C. to the boiling point over 70 minutes. During this period, the pH of the solution was measured. The pH on attainment of the boiling point is reported in the following use experiments as a measure of the effectiveness of the compounds.

Use Example A

Using 0.69 g of the product of Preparation Example 4, a final pH of 4.7 was reached. Using 0.80 g of the product of Preparation Example 3, a final pH of 5.1 was reached. Using 1.05 g of a similarly prepared condensation product of lactic acid and ethylene glycol in a molar ratio of 1:1 according to Preparation Example 1, the pH only decreased to 5.6.

Use Example B

Using 0.76 g of the product of Preparation Example 6, a final pH of 4.8 was reached. Using 0.97 g of the product of Preparation Example 5, a final pH of 5.4 was reached. Using 1.49 g of a similarly prepared condensation product of lactic acid and diethylene glycol in a molar ratio of 1:1 according to Preparation Example 2, the pH only decreased to 5.8.

Use Example C

Using 0.60 g of the product according to Preparation Example 8, a final pH of 4.0 was reached. Using 0.71 g of the product according to Preparation Example 7, a final pH of 4.3 was reached.

Use Example D

Using 0.71 g of the product according to Preparation Example 10, a final pH of 4.3 was reached. Using 0.85 g of the product according to Preparation Example 9, a final pH of 4.7 was reached.

Use Example E

Using 0.82 g of the product according to Preparation Example 13, a final pH of 4.9 was reached. Using 0.94 g of the product according to Preparation Example 12, a final pH of 5.0 was reached. Using 1.27 g of the product according to Preparation Example 11, the pH only decreased to 5.5.

What is claimed is:

1. A textile finishing process comprising the steps of:
providing a mixture of products formed by condensation of a first and a second compound wherein each mole of the first compound is condensed with at least two moles of the second compound, the first compound is selected from the group consisting of: a glycol, a diglycol, a higher glycol, and a glycerol and the second compound is an α-hydroxycarboxylic acid of the general formula (I)

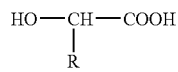

where R is hydrogen or a $C_{1-3}$ alkyl group, as an acid donor in textile finishing processes;
providing a textile material; and
applying the mixture to the textile material.

2. The process according to claim 1 where R is hydrogen or methyl.

3. The process according to claim 1, where the diglycol is diethylene glycol and the α-hydroxycaboxylic acid is lactic acid.

4. The process according to claim 1, where the textile finishing process is a dyeing process further comprising the steps of:
providing a dye;
where both the dye and the mixture are applied to the textile material.

5. The process according to claim 4, where the textile material is polyamide fiber.

6. The process according to claim 4, where the textile material is wool.

7. A process for regulating the pH in a textile finishing process comprising the steps of providing a mixture of products formed by condensation of a first and a second compound wherein each mole of the first compound is condensed with at least two moles of the second compound, the first compound is selected from the group consisting of a glycol, a diglycol, a higher glycol, and a glycerol and the second compound is an α-hydroxycarboxylic acid of the general formula (I)

where R is hydrogen or a $C_{1-3}$ alkyl group;
and adding the mixture to the textile finishing product to regulate the pH.

8. The process according to claim 1, wherein the first compound is selected from the group consisting of ethylene glycol, a diglycol and a higher glycol.

9. The process according to claim 1, wherein the first compound is selected from the group consisting of a diglycol and a higher glycol.

10. The process according to claim 7, wherein the first compound is selected from the group consisting of ethylene glycol, a diglycol and a higher glycol.

11. The process according to claim 7, wherein the first compound is selected from the group consisting of a diglycol and a higher glycol.

12. A textile finishing process comprising the steps of:
providing a mixture of products formed by the condensation of a first and a second compound wherein each mole of the first compound is condensed with at least two moles of the second compound, the first compound is a glycerol and the second compound is an α-hydroxycarboxylic acid of the general formula (I)

where R is hydrogen or a $C_{1-3}$ alkyl group, as an acid donor in textile finishing processes;
providing a textile material; and
applying the mixture to the textile material.

13. A process according to claim 7, wherein the first compound is glycerol.

* * * * *